(12) United States Patent
Meridew

(10) Patent No.: US 7,572,283 B1
(45) Date of Patent: Aug. 11, 2009

(54) SOFT TISSUE RIVET AND METHOD OF USE

(75) Inventor: Jason D Meridew, Syracuse, IN (US)

(73) Assignee: Biomet Sports Medicine, LLC, Warsaw, IN (US)

( * ) Notice: Subject to any disclaimer, the term of this patent is extended or adjusted under 35 U.S.C. 154(b) by 875 days.

(21) Appl. No.: 11/006,418

(22) Filed: Dec. 7, 2004

(51) Int. Cl.
*A61B 17/86* (2006.01)

(52) U.S. Cl. ............... 606/321; 606/326; 606/327; 606/328; 606/232

(58) Field of Classification Search ........... 606/232, 606/321, 324, 326, 327, 328, 320; 623/13.11, 623/13.14; 411/80.1, 80.5, 34, 59
See application file for complete search history.

(56) References Cited

U.S. PATENT DOCUMENTS

| | | | |
|---|---|---|---|
| 4,409,974 A | 10/1983 | Freedland | |
| 4,738,255 A | 4/1988 | Goble et al. | |
| 5,167,665 A | 12/1992 | McKinney | |
| 5,258,016 A | 11/1993 | DiPoto et al. | |
| 5,464,427 A | 11/1995 | Curtis et al. | |
| 5,501,695 A | 3/1996 | Anspach, Jr. et al. | |
| 5,531,792 A | 7/1996 | Huene | |
| 5,601,558 A | 2/1997 | Torrie et al. | |
| 5,645,589 A | 7/1997 | Li | |
| 5,649,963 A | 7/1997 | McDevitt | |
| 5,713,903 A | 2/1998 | Sander et al. | |
| 5,720,753 A | 2/1998 | Sander et al. | |
| 5,725,529 A | 3/1998 | Nicholson et al. | |
| 5,725,541 A * | 3/1998 | Anspach et al. ............ 606/151 |
| 5,741,282 A | 4/1998 | Anspach, III et al. | |
| 5,814,071 A | 9/1998 | McDevitt et al. | |
| 5,911,721 A | 6/1999 | Nicholson et al. | |
| 5,928,244 A | 7/1999 | Tovey et al. | |
| 5,935,129 A | 8/1999 | McDevitt et al. | |
| 5,941,901 A | 8/1999 | Egan | |
| 5,968,044 A | 10/1999 | Nicholson et al. | |
| 6,056,751 A | 5/2000 | Fenton, Jr. | |
| 6,129,762 A | 10/2000 | Li | |
| 6,149,669 A | 11/2000 | Li | |
| 6,210,376 B1 | 4/2001 | Grayson | |
| 6,214,012 B1 | 4/2001 | Karpman et al. | |
| 6,319,269 B1 | 11/2001 | Li | |
| 6,464,706 B1 | 10/2002 | Winters | |
| 6,517,564 B1 | 2/2003 | Grafton et al. | |

(Continued)

OTHER PUBLICATIONS

Cannulated ArthroRivet™ Anchor brochure, Arthrotek® Aug. 2003.

(Continued)

*Primary Examiner*—Eduardo C Robert
*Assistant Examiner*—Andrew Yang
(74) *Attorney, Agent, or Firm*—Harness, Dickey

(57) ABSTRACT

A method and apparatus for reattaching soft tissue to a selected boney structure using a rivet. Generally, a rivet having first portion and a second portion is provided to fully secure a soft tissue in the boney structure. The first portion of the rivet retains the soft tissue via a suture which is threaded through the first portion. The second portion of the rivet has at least one expanding member which engages the boney structure upon contact with the first portion of the rivet. Thus, the soft tissue is fully secured to the boney structure, ensuring proper healing.

15 Claims, 3 Drawing Sheets

U.S. PATENT DOCUMENTS

| | | | |
|---|---|---|---|
| 6,524,316 | B1 | 2/2003 | Nicholson et al. |
| 6,554,830 | B1 | 4/2003 | Chappius |
| 6,565,572 | B2 | 5/2003 | Chappius |
| 6,599,295 | B1 | 7/2003 | Tornier et al. |
| 6,645,227 | B2 | 11/2003 | Fallin et al. |
| 6,652,561 | B1 | 11/2003 | Tran |
| 6,660,023 | B2 | 12/2003 | McDevitt et al. |
| 6,994,725 | B1* | 2/2006 | Goble ............... 623/13.14 |
| 7,037,324 | B2* | 5/2006 | Martinek ............... 606/232 |
| 2001/0051807 | A1 | 12/2001 | Grafton |
| 2002/0095180 | A1* | 7/2002 | West et al. ............... 606/228 |
| 2003/0144667 | A1 | 7/2003 | Enayati |
| 2004/0138707 | A1 | 7/2004 | Greenhalgh |
| 2004/0193167 | A1* | 9/2004 | Tucciarone et al. ............ 606/73 |
| 2005/0015059 | A1 | 1/2005 | Sweeney |
| 2005/0137707 | A1 | 6/2005 | Malek |

OTHER PUBLICATIONS

Cannulated ArthroRivet™, Arthrotek® Inventing the Future of Arthroscopy, print out of web site http://www.arthrotek.com/prodpage.cfm?c=0A05&p=0102 (printed Dec. 12, 2006) Copyright 2005, Arthrotek, Inc.

* cited by examiner

SOFT TISSUE RIVET AND METHOD OF USE

FIELD

The present invention relates generally to structures and methods for repairing soft tissue, and particularly to a method and apparatus for a soft tissue rivet.

BACKGROUND

Various procedures may be performed to repair soft tissue in the body. For example, tendons that attach muscle to bone or ligaments that attach bones to other bones may need to be repaired or replaced for various reasons. Specifically, an injury to a ligament in the leg for example, may require the ligament to be replaced. Alternatively, a tendon from a muscle may simply be loosened from its attachment point and need to be reattached without the necessity of a replacement.

Generally, it is known to fix the soft tissue to a selected area on the bone by providing a suture through a selected portion of the soft tissue while securing the other end of the suture to a selected area on the bone. Various structures and methods, such as soft tissue suture anchors, can be provided to anchor or hold the suture in the selected bone area. Typical soft tissue suture anchors may require the placement of the soft tissue suture anchor into the bone prior to the engagement of the soft tissue with the suture anchor. This procedure may be time consuming and require precise placement. Therefore, it may be desirable to provide a soft tissue attachment mechanism that may substantially simplify the reattachment or replacement of soft tissue during a surgical procedure.

SUMMARY

A method and apparatus for reattaching soft tissue to a pre-selected boney structure using an assembly, such as a rivet. A rivet may have a first portion and a second portion that is provided to fully secure a soft tissue in the boney structure. The first portion of the rivet retains the soft tissue via a suture which is threaded through the first portion. The second portion of the rivet has at least one expanding member that may engage the boney structure or portion upon contact with the first portion of the rivet. Thus, the soft tissue is fully secured to the boney structure, ensuring proper healing.

A device for attaching soft tissue to a pre-selected area of a boney structure is provided. The device has a bullet operable to receive a suture to engage the soft tissue and a sleeve operable to retain the bullet in the pre-selected area of boney structure via at least one expanding member. A guide pin slideably engaged with the bullet and the sleeve is operable to engage the sleeve with the bullet. The soft tissue may be attached to the device prior to insertion in the boney structure.

A device for attaching soft tissue to a pre-selected area of a boney structure including a first portion operable to retain a section of the soft tissue is provided. The device may further include a second portion operable to retain the first portion in the pre-selected area of boney structure via an expanding member. A guide pin is slideably engaged with the first portion and the second portion and extends beyond the first portion to pierce the soft tissue prior to the insertion of the soft tissue in the boney structure.

A method for attaching a soft tissue to a pre-selected area of a boney structure including forming a cavity in the boney structure for receipt of an anchor assembly is provided. The soft tissue may be coupled to a first portion of the anchor assembly and the first portion of the anchor assembly may be disposed in the cavity. A second portion of the anchor assembly is pushed along a guide pin to secure the first portion of the anchor assembly in the cavity.

Further areas of applicability of the present invention will become apparent from the detailed description provided hereinafter. It should be understood that the detailed description and specific examples, while indicating various embodiments of the invention, are intended for purposes of illustration only and are not intended to limit the scope of the invention.

BRIEF DESCRIPTION OF THE DRAWINGS

The present invention will become more fully understood from the detailed description and the accompanying drawings, wherein.

DETAILED DESCRIPTION OF VARIOUS EMBODIMENTS

The following description of various embodiments is merely exemplary in nature and is in no way intended to limit the invention, its application, or uses. Although the following description is related generally to a soft tissue anchor or rivet that can be positioned in a pre-drilled hole, that is a hole provided in a boney structure for acceptance of the soft tissue rivet. It will be understood that a soft tissue rivet including an impacting tip or self-drilling thread may be provided as well. Moreover, it will be understood that the soft tissue rivet, as described and claimed herein, can be used with any appropriate surgical procedure. Also, an anchor or rivet will be understood to refer to any appropriate assembly or device for anchoring a portion to a boney structure. Moreover, the anchor need not be positioned only in a boney structure. Therefore, it will be understood that the following discussions is not intended to limit the scope of the appended claims.

Figure 1:
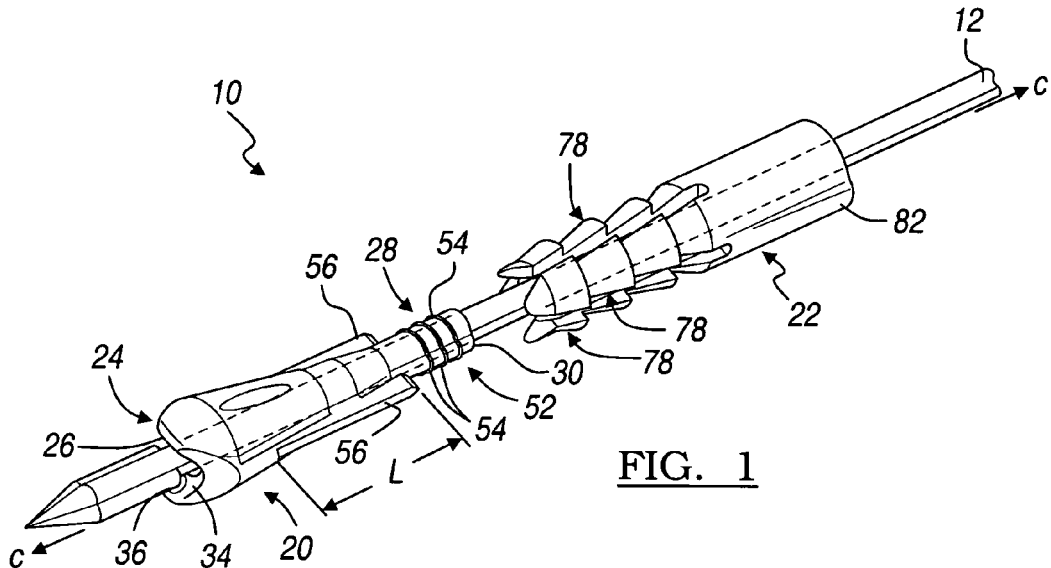
FIG. 1 is a perspective view of an soft tissue rivet according to various embodiments.
Figures 3, 4:
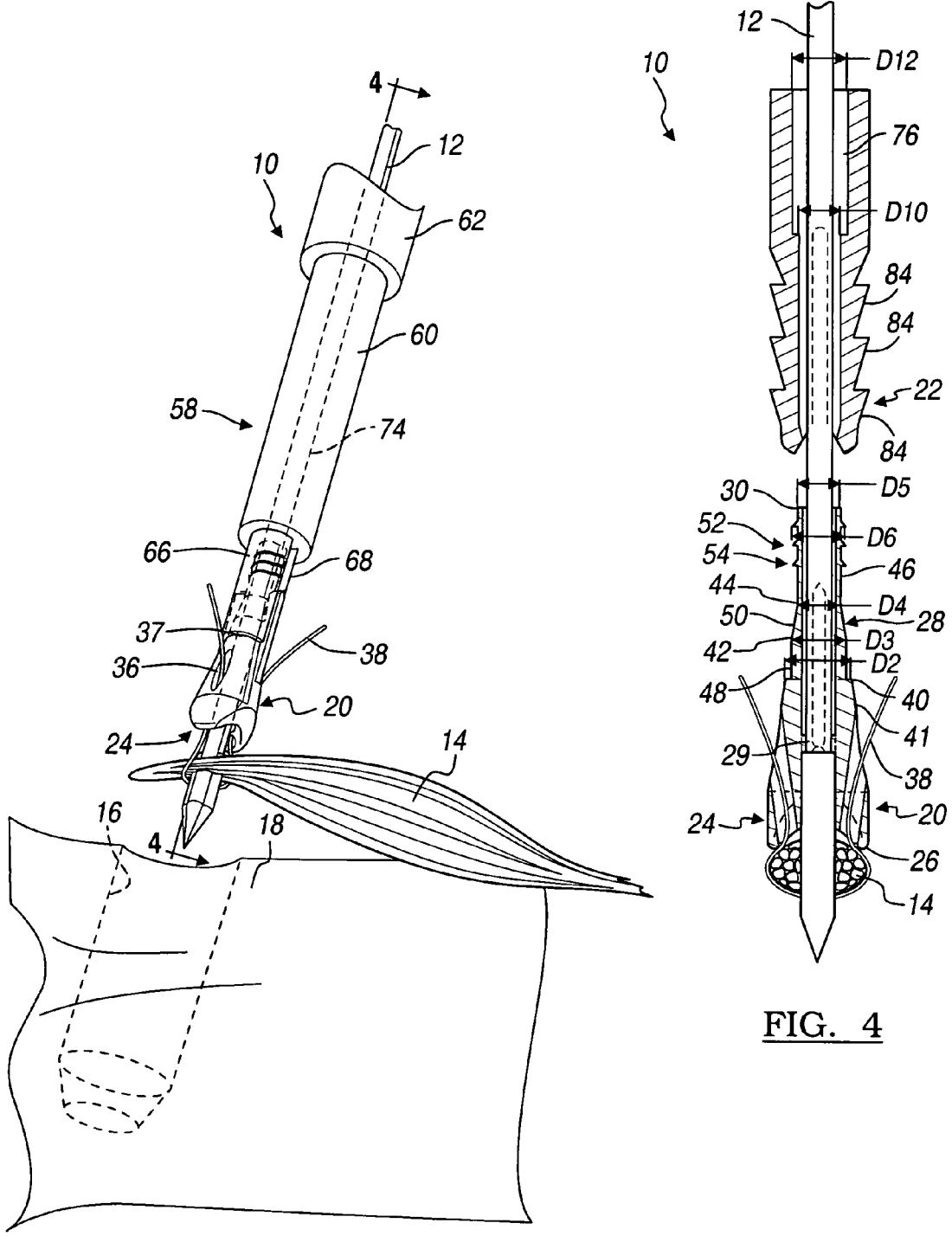
FIG. 3 is an environmental view of a use of the soft tissue rivet prior to insertion into a boney structure according to various embodiments.
FIG. 4 is a cross-sectional view taken along line 4-4 of FIG. 3.

With reference to FIGS. 1 and 3, a soft tissue rivet or anchor assembly 10 is illustrated. The rivet 10 may be operable with a guide pin 12 to secure a soft tissue portion 14 in a pre-drilled hole 16 in a boney structure 18. The rivet 10 may include a first portion or bullet 20 and a second portion or sleeve 22. Briefly, the bullet 20 may be provided to engage and position a soft tissue portion in a first instance. The bullet 20 may also interact with the sleeve 22 to hold the soft tissue in a selected position. It will be understood the bullet 20 may be any member that may be able to interact with the sleeve 22, or any appropriate member, to position a soft tissue portion in a selected manner. The bullet 20 and the sleeve 22 are merely exemplary and not intended to be limiting.

Figure 2:
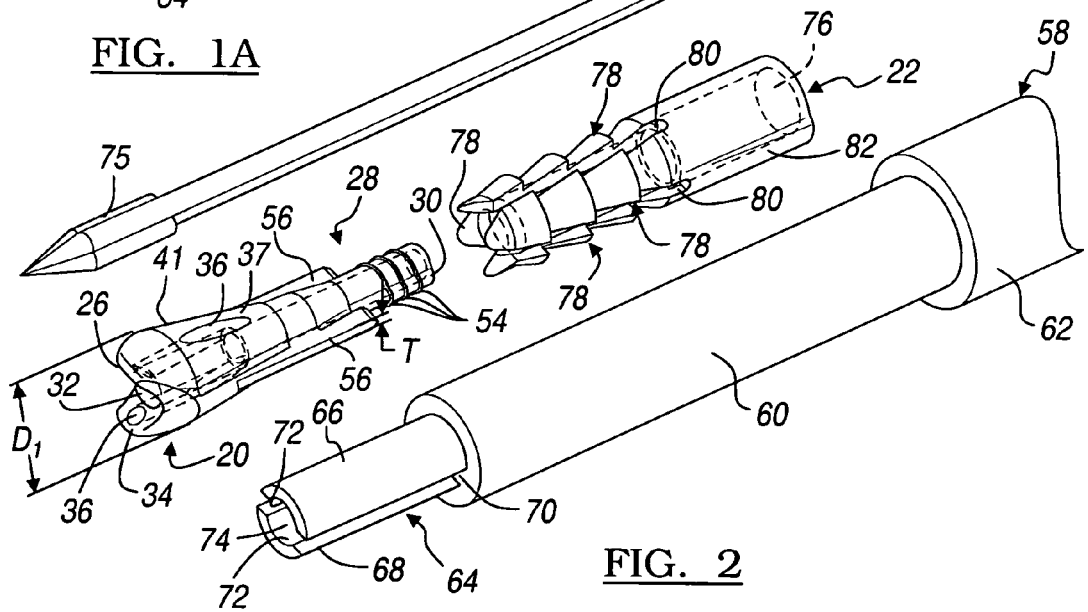
FIG. 2 is an exploded view of a kit for the soft tissue rivet of FIG. 1.

With continuing reference to FIGS. 1 and 3 and additional reference to FIGS. 2 and 4, the bullet 20 includes a generally cup-shaped section 24 at a distal end 26 and a tapered section 28 at a proximal end 30. The cup-shaped section 24 is generally displaced from the tapered section 28 via a stepped portion 29 formed in the bullet 20. The bullet 20 may further include a bore 32 which extends through the cup-shaped section 24 and tapered section 28 for receipt of the guide pin 12 therethrough. The bullet 20 may be molded from a resorbable material, such as, for example, Lactosorb®, however, it will be understood that other types of biocompatible materials and other methods of forming could be used. For example, the bullet 20 may be formed of other polymers or of metal portions.

Figure 1A:
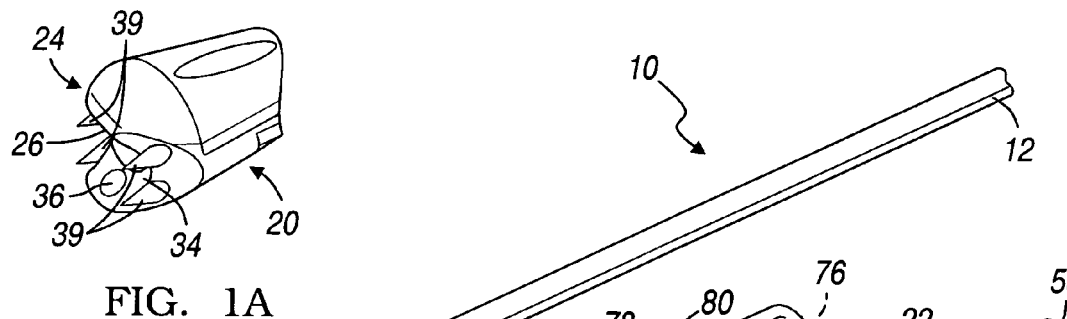
Figure 3A:
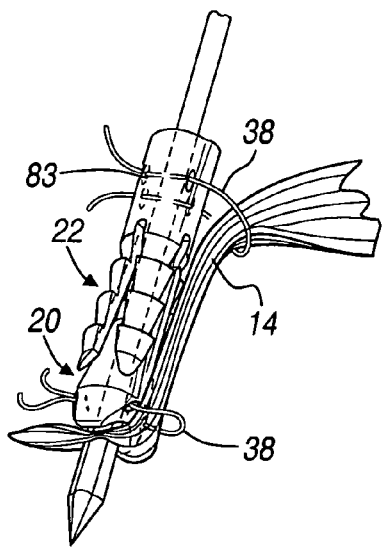

The cup-shaped section 24 may be configured for receipt of the soft tissue 14. The cup-shaped section 24 may define a diameter D1 which is generally the largest diameter of the bullet 20. The cup-shaped section 24 has a surface 34 which abuts the soft tissue 14 when the rivet 10 is fully secured in the boney structure 18, as will be described in greater detail below. The bullet 20 further includes a pair of formed eyelets 36 for receipt of flexible member or strand 38, such as a suture, therethrough. The eyelets 36 may be formed along a side 37 of the bullet 20, as shown in FIGS. 3 and 4, or may be formed transverse on the bullet 20, as shown in FIG. 3A. The flexible strand 38 secures the soft tissue 14 to the surface 34 of the cup-shaped section 24. Although the cup-shaped section 24 is described herein as being cup-shaped, it will be understood that other shapes could be used depending on the particular soft tissue configuration, such as, for example, box-shaped. The cup-shaped section 24 may also be formed of a deformable material to substantially mold to the soft tissue in site. Further, the cup-shaped section 24 may include at least one or multiple projections 39, as illustrated in FIG. 1A, to further secure the soft tissue (not shown) to the cup-shaped section 24.

With reference back to FIGS. 1, 2, 3 and 4, the tapered section 28 of the bullet 20 may include a first shoulder 40, second shoulder 42 and a third shoulder 44 adjacent to an end portion 46. The first shoulder 40 is separated from the cup-shaped section 24 by a tapered area 41 and has a diameter D2 that is generally smaller than the diameter D1 of the cup-shaped section 24. The first shoulder 40 is coupled to the second shoulder 42 by a cylindrical section 48. The second shoulder 42 is coupled to the third shoulder 44 by a tapered area 50. The diameter D2 of the first shoulder 40 is generally greater than a diameter D3 of the second shoulder 42. A diameter D4 of the third shoulder 44 is generally smaller than the diameter D3 of the second shoulder 42, such that the second shoulder 42 and third shoulder 44 form a generally tapered section which ends at the first shoulder 40. The end portion 46 of the tapered section 28 has a diameter D5 which is generally equal to the diameter D4 of the third shoulder 44.

It will be understood, however, that only appropriate configuration may be provided to extend from the distal end 28 of the bullet 20. As described herein, the bullet 20 interacts with the second portion 22 and any configuration may be provided for such an interaction. The end portion 46 further includes at least one grip surface 52 to couple the bullet 20 to the sleeve 22. The grip surface 52 may include an annular protrusion 54, and in this exemplary embodiment, the end portion 46 includes three annular protrusions 54 having a diameter D6 which interact or mate with the sleeve 22. Although this embodiment includes three annular protrusions 54, it will be understood that the grip surface 52 could be configured in any manner that may assist in coupling or interconnecting the bullet 20 to the sleeve 22, such as, for example, barbs. The shape of the tapered section 28 from the first shoulder 40 to the end portion 46 defines a surface for mating the bullet 20 with the sleeve 22 as will be described in greater detail below.

The tapered section 28 may also include a pair of formed flanges 56 having a thickness T spaced about a centerline C of the bullet 20. The flanges 56 are generally triangular and extend a length L from the cup-shaped section 24 to the third shoulder 44 of the tapered section 28. The flanges 56 may provide a locating point for an instrument 58. The instrument 58 is removably coupled to the bullet 20 to insert the bullet 20 with the attached soft tissue 14 into the pre-drilled hole 16 in the boney structure 18.

The instrument 58 may be cylindrical in shape with a body 60 coupled to a handle portion 62. The body 60 is further coupled to an attachment section 64 for receipt of the flanges 56 from the bullet 20 therein. Specifically, the attachment section 64 has a first cupped flange 66 and a second cupped flange 68 separated by a slot 70. The first and second cupped flanges 66, 68 have an interior surface 72 that is configured to slideably engage the tapered section 28 of the bullet 20. The instrument 58 may further define a throughbore 74 for receipt of the guide pin 12 therethrough.

The guide pin 12 is configured to slideably engage the throughbore 74 of the instrument 58 when the instrument 58 is attached to the bullet 20. The guide pin 12 extends through the bore 32 of the bullet 20 and may extend beyond the cup-shaped section 24 to pierce the soft tissue 14. The guide pin 12 may also include a stepped portion 75 to engage the cup-shaped section 24, as will be discussed in greater detail below. The guide pin 12 can be made of any suitable biocompatible corrosive resistant material, such as, for example, surgical steel and may be a K-wire or other appropriate member. In this regard, the guide pin 12 need not be made of the same material as the bullet 20. In addition, the guide pin 12 is configured to slideably engage the sleeve 22. The slideable engagement of the guide pin 12 with the sleeve 22 facilitates the engagement of the sleeve 22 with the bullet 20.

The sleeve 22 includes a throughbore 76 to allow the guide pin 12 therethrough. The sleeve 22 is typically made from a resorbable material, such as, for example, Lactosorb®, however other suitable materials could be employed such as other polymers or metals. The sleeve 22 may include one or a plurality of expanding members 78 defined or separated by a slot 80 in an annular body 82. The annular body 82 may further include formed eyelets 83 for receipt of a suture 38 therethrough to couple the soft tissue 14 to the sleeve 22, as shown in FIG. 3A. With reference back to FIGS. 1, 2, 3 and 4, the expanding members 78 are hingedly coupled to the annular body 82 to enable the expanding members 78 to move and secure the sleeve 22 in the pre-drilled hole 14. More specifically, the throughbore 76 has a first diameter D10 associated with the expanding members 78 and a second diameter D12 associated with the annular body 82. The first diameter D10 of the throughbore 76 is approximately equal to the diameter D5 of the end section 46 but smaller than the diameter D6 of the annular protrusion 54. In addition, the first diameter D10 of the throughbore 76 is smaller than the diameter D3 of the second shoulder 44 and diameter D2 of the first shoulder 40, such that as the sleeve 22 is slid over the bullet 20, the expanding members 78 are forced open by the tapered section 28 of the bullet 20. The expanding members 78 may include at least one barb or engaging portion 84 for engaging or securing the sleeve 22 in the boney structure 18. In this exemplary embodiment, the expanding members 78 include three barbs 84 for engagement with the boney structure 18.

Figure 5:
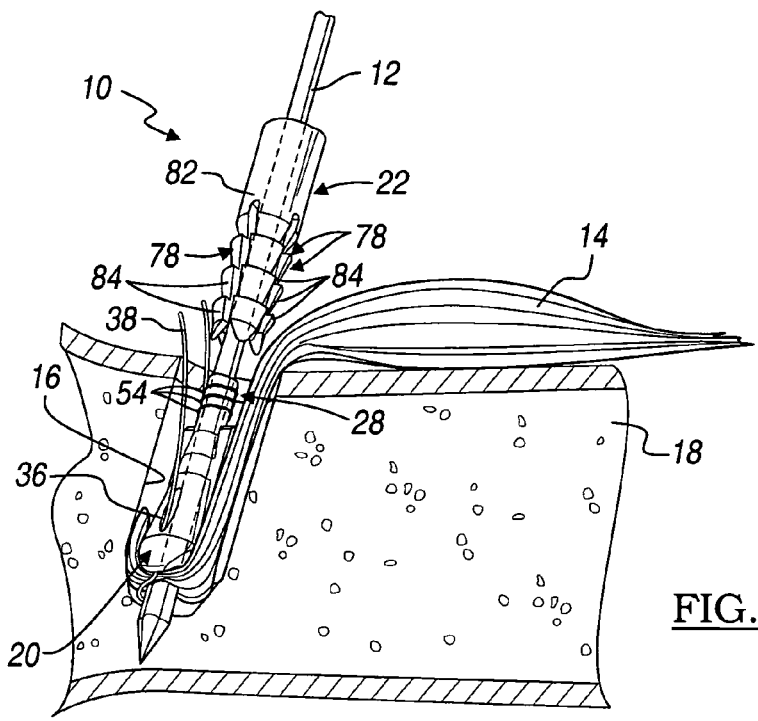
FIG. 5 is an environmental view illustrating the soft tissue rivet prior to engagement in the boney structure.
Figure 6:
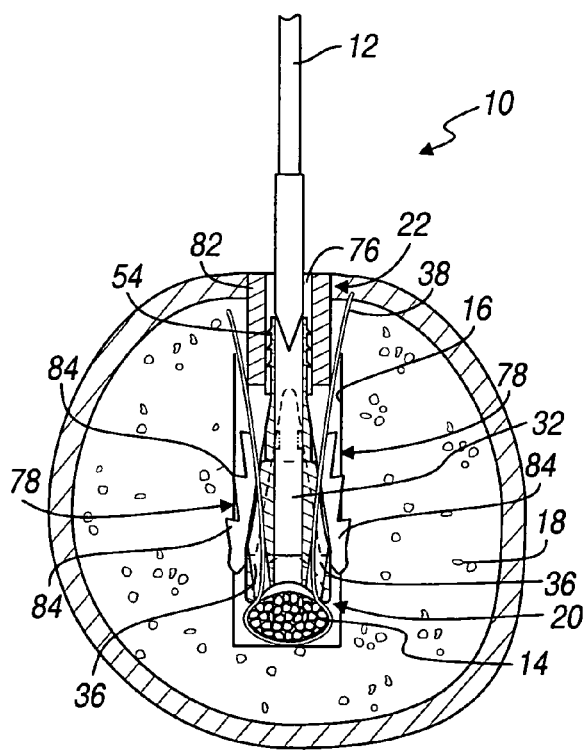
FIG. 6 is an environmental view of the soft tissue rivet in a fully engaged in the boney structure.

With continuing reference to FIGS. 3 and 4, and additional reference to FIGS. 5 and 6 a method according to various embodiments for using the device 10 is illustrated. After the hole 16 has been drilled into the boney structure 18, the flexible strand 38 can be wrapped around the soft tissue 14 and threaded through the eyelets 36 of the bullet 20. The flexible strand 38 may be pulled tight to the bullet 20 causing the soft tissue 14 to be pierced by the guide pin 12. The shape of the bullet 20 allows for minimal contact of the flexible strand 38 with the boney structure 18 to protect the flexible strand 38 during the insertion of the bullet 20 into the boney structure 18. In particular, the configuration of the eyelets 36 enables at least a portion of the flexible strand 38 to pass through at least a portion of the bullet 20. The positioning of the flexible strand 38 in the bullet 20 may assist in ensuring that the flexible strand 38 is not exposed to possible sources of abrasion. In addition, the placement of the flexible strand 38 within the bullet 20 ensures that the flexible strand 38 does not interfere with the operation of the sleeve 22.

Once the soft tissue 14 is secured to the bullet 20, the instrument 58 is attached to the bullet 20. Specifically, the first and second cupped flanges 66, 68 removably engage the bullet 20 to enable a surgeon to then insert the bullet 20 with the connected soft tissue 14 and guide pin 12 into the pre-drilled hole 16 in the boney structure 18.

After the bullet 20 has been inserted into the pre-drilled hole 16, the instrument 58 is detached from the bullet 20. The sleeve 22 may be placed on the guide pin 12 and pushed down the guide pin 12 until the expanding members 78 firmly engage the boney structure 18 and the annular protrusions 54 have secured the sleeve 22 to the bullet 20. The sleeve 22 is generally configured such that when the sleeve 22 is fully engaged with the boney structure 18, the sleeve 22 does not extend beyond a surface 86 of the boney structure 18. Once the rivet 10 is fully secured in the boney structure 16, the guide pin 12 may be removed by applying a retractive force F. The removal of the guide pin 12 causes the stepped portion 75 of the guide pin 12 to engage the stepped portion 29 of the bullet 20. The continued application of the retractive force F causes the stepped portion 75 of the guide pin 12 to shear the stepped portion 29 from the bullet 20, resulting in the bore 32 becoming devoid of the stepped portion 29 which previously separated the cup-shaped section 24 from the tapered section 28. The shearing of the stepped portion 29 of the bullet 20 ensures that the expanding members 78 are firmly engaged in the boney structure 18.

The anchor or rivet 10 may allow for a more efficient and quick surgical reattachment of a soft tissue portion. Thus, the rivet 10 may decrease the time needed to complete a soft tissue reattachment or repair. The ability of the rivet 10 to securely engage boney structures 18 ensures the soft tissue 16 is held close to the bone for improved healing time.

The description of the invention is merely exemplary in nature and, thus, variations that do not depart from the gist of the invention are intended to be within the scope of the invention. Such variations are not to be regarded as a departure from the spirit and scope of the invention.

What is claimed is:

1. A method for attaching a soft tissue to a boney structure, the method comprising:
   forming a cavity in the boney structure for receipt of an anchor assembly;
   piercing the soft tissue with a guide pin extending beyond a surface of the first portion of the anchor assembly;
   coupling the soft tissue to a first portion of the anchor assembly;
   disposing the first portion of the anchor assembly in the cavity;
   engaging a second portion of the anchor assembly with the first portion of the anchor assembly with the attached soft tissue in the cavity; and
   securing the first portion in the boney structure by applying a retractive force to the guide pin to fully expand an expandable member, the application of the retractive force to the guide pin shearing a stepped portion on the first portion of the anchor assembly when the expandable member is fully expanded.

2. The method of claim 1 wherein the process of coupling the soft tissue to a first portion of the anchor assembly further comprises:
   engaging the soft tissue with a flexible member received through an eyelet in the first portion of the anchor assembly; and
   pulling the flexible member until the soft tissue is adjacent the surface of the first portion of the anchor assembly.

3. The method of claim 1 wherein the process of coupling the soft tissue to a first portion of the anchor assembly further comprises:
   piercing the soft tissue with a guide pin extending beyond a surface of the first portion of the anchor assembly.

4. The method of claim 1 further comprising:
   using an instrument to dispose the first portion of the anchor assembly in the cavity;
   engaging the instrument with a guide pin;
   coupling a first end of the instrument to a tapered section of the first portion of the anchor assembly; and
   removing the instrument from the guide pin and first portion of the anchor assembly.

5. The method of claim 1 further comprising:
   pushing the second portion of the anchor assembly onto a tapered section of the first portion of the anchor assembly to cause an expanding portion on the second portion of the anchor assembly to engage the boney structure.

6. The method of claim 1 further comprising:
   removing a guide pin from the anchor assembly while the second portion of the anchor assembly is engaged with the first portion of the anchor assembly.

7. The method of claim 1 further comprising:
   engaging the first portion with the bony structure to at least partially shield a suture from engagement with the bony structure.

8. A method for attaching a soft tissue to a boney structure, the method comprising:
   forming a cavity in the boney structure for receipt of an anchor assembly;
   threading a flexible strand through a first portion of the anchor assembly;
   securing the soft tissue with the flexible strand;
   pulling the flexible strand such that a guide pin inserted through the first portion of the anchor assembly pierces the soft tissue;
   inserting the first portion of the anchor assembly and the guide pin into the cavity;
   passing a second portion of the anchor assembly over the guide pin into the cavity;
   retracting the guide pin from the cavity to deploy the second portion of the anchor assembly;
   wherein inserting the first portion of the anchor assembly and the guide pin into the cavity further comprises:
      coupling an instrument to the first portion of the anchor assembly;
      inserting the first portion of the anchor assembly and the guide pin into the cavity with the instrument; and
      removing the instrument from the first portion of the anchor assembly prior to passing the second portion of the anchor assembly over the guide pin.

9. The method of claim 8, wherein passing the second portion of the anchor assembly over the guide pin into the cavity further comprises:
   passing the second portion of the anchor assembly over the guide pin until the second portion of the anchor assembly is coupled to the first portion of the anchor assembly.

10. The method of claim 9, wherein passing the second portion of the anchor assembly over the guide pin further comprises:
 at least partially expanding expandable members of the second portion of the anchor assembly.

11. The method of claim 10, wherein retracting the guide pin from the cavity to deploy the second portion of the anchor assembly further comprises:
 applying a retractive force to the guide pin to fully expand the expandable members, the application of the retractive force to the guide pin shearing a stepped portion on the first portion of the anchor assembly when the expandable members are fully expanded.

12. The method of claim 8, wherein passing the second portion of the anchor assembly over the guide pin into the cavity further comprises:
 positioning the second portion of the anchor assembly within the cavity such that the second portion of the anchor does not extend beyond a surface of the boney structure.

13. The method of claim 8, wherein threading the flexible strand through the first portion of the anchor assembly further comprises:
 threading the flexible strand through at least one eyelet in the first portion of the anchor assembly.

14. The method of claim 8, wherein threading the flexible strand through the first portion of the anchor assembly further comprises:
 threading the flexible strand through at least a portion of the first portion of the anchor assembly to protect at least a portion of the flexible strand from contact with the boney structure.

15. A method for attaching a soft tissue to a boney structure, the method comprising:
 forming a cavity in the boney structure for receipt of an anchor assembly;
 threading a flexible strand through at least one eyelet in a first portion of the anchor assembly;
 securing the soft tissue with the flexible strand;
 pulling the flexible strand such that a guide pin inserted through the first portion of the anchor assembly pierces the soft tissue;
 inserting the first portion of the anchor assembly and the guide pin into the cavity;
 passing a second portion of the anchor assembly over the guide pin until the second portion of the anchor assembly is coupled to the first portion of the anchor assembly, the second portion of the anchor assembly including at least one expandable member;
 retracting the guide pin to fully expand the at least one expandable member of the second portion; and
 shearing a stepped portion of the first portion of the anchor assembly when the at least one expandable member is fully expanded.

* * * * *